United States Patent [19]

Spillman, Jr.

[11] Patent Number: 4,900,921
[45] Date of Patent: Feb. 13, 1990

[54] SYSTEM AND METHOD FOR OPTO-ACOUSTIC LIQUID QUANTITY MEASUREMENT AND TRANSDUCER THEREFOR

[75] Inventor: William B. Spillman, Jr., Charlotte, Vt.

[73] Assignee: Simmonds Precision Products, Inc., Wilmington, Del.

[21] Appl. No.: 246,103

[22] Filed: Sep. 19, 1988

[51] Int. Cl.$^4$ .............................................. H01J 5/16
[52] U.S. Cl. .................................... 250/227; 250/577
[58] Field of Search ............... 250/227, 231 R, 231 P, 250/577; 73/290 V, 293

[56] References Cited

U.S. PATENT DOCUMENTS

| | | | |
|---|---|---|---|
| 4,493,996 | 1/1985 | Sterling | 250/227 |
| 4,567,451 | 1/1986 | Greenwood | 250/227 |
| 4,677,305 | 6/1987 | Ellinger | 250/577 |
| 4,772,786 | 9/1988 | Langdon | 250/227 |

Primary Examiner—David C. Nelms
Attorney, Agent, or Firm—Dale R. Lovercheck

[57] ABSTRACT

The system and method provide an electrically passive optically controlled acoustic transceiver system which measures the quantity of a liquid, such as aircraft fuel, in a tank. Pulsed electromagnetic radiation, such as light or infrared radiation, is guided through an optical fiber and impinged upon a flexible member adapted to flex when heated and transmit acoustic pulses. An optical fiber detector, is used to monitor the acoustic pulses reflected from the liquid level in a fuel tank. The system is electrically passive and does not require or use electrical power at the sensing location.

26 Claims, 2 Drawing Sheets

SYSTEM AND METHOD FOR OPTO-ACOUSTIC LIQUID QUANTITY MEASUREMENT AND TRANSDUCER THEREFOR

The invention relates to acoustic liquid quantity gauging. More particularly, the invention provides electrically passive acoustic transmission and detection for liquid quantity gauging. The invention is useful for fuel quantity gauging in aircraft fuel tanks.

In accordance with the invention, an electrically passive optically controlled acoustic transceiver system is provided which measures the quantity of a liquid, such as aircraft fuel, in a tank. Pulsed electromagnetic radiation, such as light or infrared radiation, is guided through an optical fiber and impinged upon a flexible member of an opto-acoustic transducer. The flexible member is adapted to flex when heated. The energy of each pulse of electromagnetic radiation is rapidly absorbed as heat by the flexible member. Preferably, the flexible member is a thin semispherical shaped black-coated metal member supported to allow it to flex when heated by the pulses of electromagnetic radiation. Each flexing of the metal member initiates an acoustic pulse which is directed to travel through a liquid to an air-liquid interface from which a reflected acoustic pulse returns through the liquid to a monitoring optical fiber. The monitoring optical fiber directs light (or infrared radiation) to a detector. The travel time of each of the acoustic pulses to and from the liquid-air interface is timed by monitoring the time between initiating the acoustic pulse and detecting the return of the reflected acoustic pulse. The return of the reflected acoustic pulse is detected as a change in the properties of the transmitted light or infrared radiation.

It is an object of the invention to provide an electrically passive optically activated acoustic transmitter for use in fuel quantity gauging.

It is an object of the invention to provide an electrically passive optically activated acoustic receiver for use in fuel quantity gauging.

It is an object of the invention to provide a method of and a system for liquid quantity gauging which is electrically passive and optically activated.

Ellinger, in U.S. Pat. No. 4,677,305 (assigned to Simmonds Precision Products, Inc.) discloses an opto-acoustic fuel quantity gauging system which uses an electrically activated transducer. The opto-acoustic fluid measurement system of the present invention provides an electrically passive optically activated transducer.

Brown, D. H. "Liquid Level Measurement by Ultrasonic Ranging" Central Electricity Generating Board, (London Aug. 1976 Brown discloses the concept of an ultrasonic ranging device for measuring the liquid level in a container. An ultrasonic pulse is propagated upwardly from the bottom of the container. The propagation time between the generation of the pulse and the reception of the reflected wave is indicative of the liquid level. Skrgatic, in U.S. Pat. No. 4,580,448 discloses a system similar to that of Brown which uses an ultrasonic liquid level sensor in which an ultrasonic crystal transducer mounted exteriorly of the liquid container transmits a pulse through the container wall and the liquid and detects the reflected wave to determine liquid level.

Edelman, in U.S. Pat. 4,334,321 discloses an opto-acoustic transducer by which power-modulated light is transmitted through a fiber and absorbed to generate heat which, in turn, effects expansion and contraction of the light guide to develop sound energy. The transducer is indicated as providing an audio output of between 300 and 3300 Hz.

BRIEF DESCRIPTION OF THE INVENTION

The system and method provide an electrically passive optically controlled acoustic transceiver system which measures the quantity of a liquid, such as aircraft fuel, in a tank. Pulsed electromagnetic radiation, such as light or infrared radiation, is guided through an optical fiber and impinged upon a flexible member adapted to flex when heated and transmit acoustic pulses. An optical fiber detector, is used to monitor the acoustic pulses reflected from the liquid level in a fuel tank. The system is electrically passive and does not require or use electrical power at the sensing location.

DETAILED DESCRIPTION OF THE INVENTION

Figure 1:
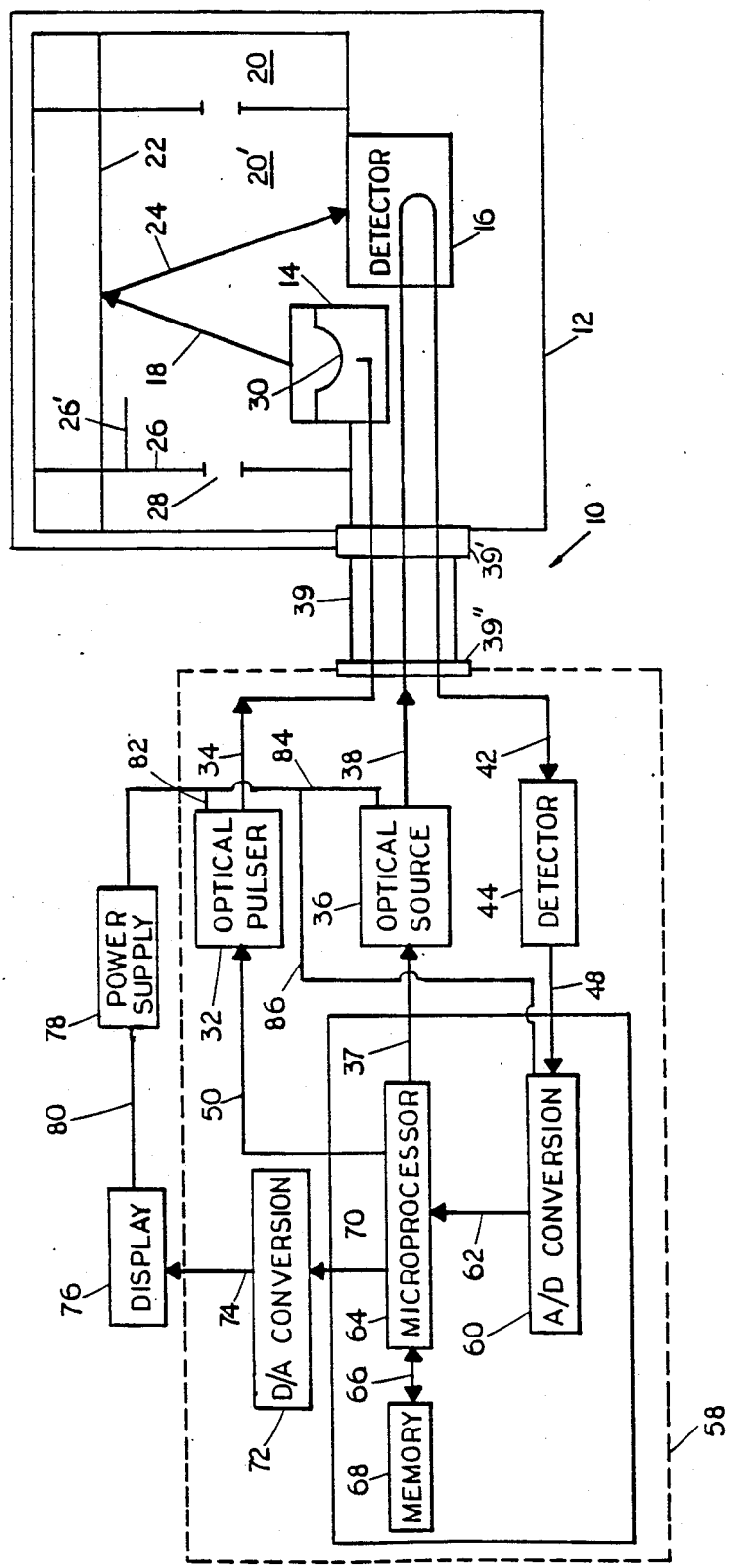
FIG. 1 is a schematic representation of an optically controlled acoustic transmission and detection system for fuel quantity gauging in accordance with the invention.
Figure 2:
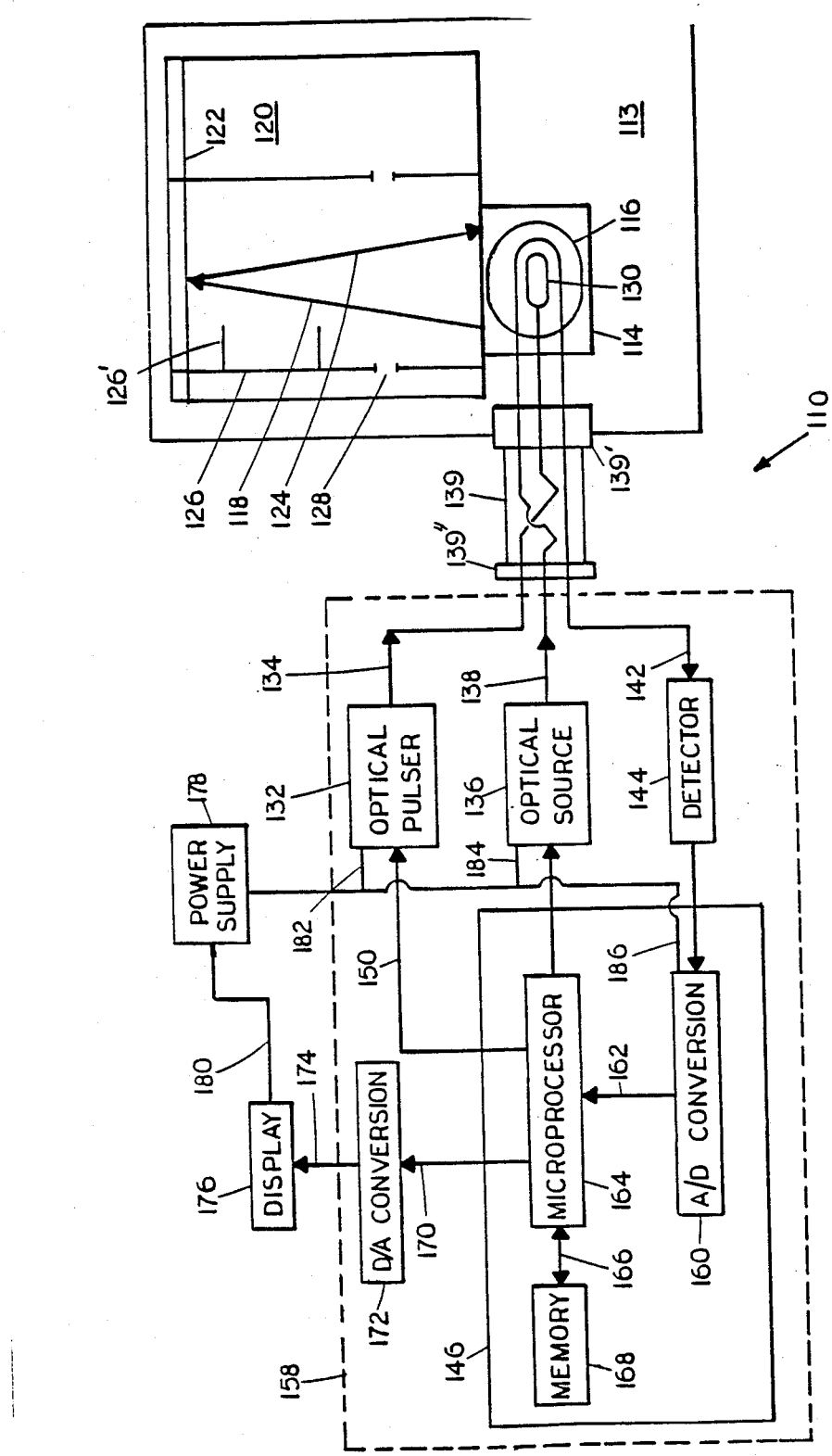
FIG. 2 is a schematic representation of an embedded optically controlled acoustic transceiver for fuel quantity gauging in accordance with the invention.

The invention is now described with reference to the drawings wherein FIGS. 1 and 2 show preferred embodiments of the invention. With more particular reference to FIG. 1, an electrically passive opto-acoustic liquid quantity gauging system 10 is shown. The electrically passive acoustic fuel quantity gauging system shown generally at 10 includes a tank 12 which supports acoustic source 14 and an acoustic detector 16, and encloses liquid fuel 20. The source 14 transmits acoustic output Pulses 18 through still fuel 20' enclosed by stillwell 26' to the liquid-air interface 22 from which acoustic reflection pulses 24 are reflected to acoustic detector 16. The stillwell 26 is supported by the tank 12 so that the pulses 18 and 24 travel through still fuel 20' which is less turbulent in flight than is the portion of fuel 20 which is outside of the stillwell 26. Stillwell 26 supports reference reflector 26'. Fuel flows freely into and out of the stillwell 26 through aperture 28.

The source 14 preferably includes a metal member 30 having a rounded or semispherical (concave or convex) shape supported to allow flexion of the rounded portion. Preferably, at least a portion of the surface of the metal member 30 is nonreflective and black. Optical pulser 32 pulses high intensity light through optical fiber 34 to the plate 30 which rapidly flexes thereby transmitting acoustic pulses 18. The pulser 32 is preferably a pulsed laser, pulsed laser diode, Q-switched laser or optically pumped Q-switched laser.

The optical source 36 transmits light through optical fiber 38 to acoustic detector 16. Reflected acoustic pulses 24 impinge upon detector 16. The detector 16 is preferably a loop 40 in optical fiber 38. The fiber 38 may be a single mode or multimode optical fiber. The optical fibers 34, 38 and 42 extend through connectors 39' and 39" and are protected by shielding 39. The output portion, 42 of fiber 38 channels the light to optical detector 44. Detector 44 is connected to signal conditioning electronics 46 by electrical conductor 48. Signal conditioning electronics 46 is connected by electrical conductor 50 to high intensity optical pulser 32. Opto-acoustic signal conditioner 58 includes pulser source 36, detector 44 and signal conditioning electronics 46. Signal conditioning electronics 46 includes analog to digital (A/D) converter 60 which is connected by electrical conductor 48 to detector 44, and by electrical conductor 62 to microprocessor 64. Microprocessor 64 sends and receives signals from memory 68 through electrical conductor 66.

Microprocessor 64 sends digital signal through conductor 70 to D/A converter 72. D/A converter 72 sends analog signals through electrical conductor 74 to display 76. Power supply 78 supplies electrical current through electrical conductor 80 to display 76. Power supply 78 supplies electrical current through electrical conductor 82 to optical pulser 32. Electrical conductor 84 is connected to power supply 78 which supplies electrical current to optical source 36. Power supply 78 supplies electrical current through electrical conductor 86 to A/D converter 60.

By detecting and indicating changes in the light signal from the optical source 36 the return of the reflection pulses is detected and used to indicate the quantity of fuel in tank 12. The detector 44, which preferably is a photodetector, receives electromagnetic radiation, such as light from the output portion 42 of optical fiber 38. It will be understood that any type of physical movement of the optical fiber 38, such as slight bending, will have an effect upon the light transmitted therethrough. Various parameters (or properties) of the light can be detected, such as back scattering sites, discontinuities, attenuation, and the like. Physical movement of the optical fiber in detector 16 is caused by the impact of the returning acoustic waves (reflection pulses) in the liquid 20' on the detector 16. This movement of the optical fiber causes changes in the properties of the light signal traveling within the optical fiber. The changes in the properties of the light in the output portion of optical fiber 42 are optical information which is converted to digital form in A/D converter 60 and fed into the microprocessor 64. The fuel quantity in tank 12 is determined in microprocessor 64 and signals representative of fuel quantity are displayed by display 70. Movement of the detector 16 is monitored by following the corresponding changes in the parameters of the light passing through the fiber 38, which are detected by detector 44 and processed in the microprocessor 64. The microprocessor 64 may send further signals to the optical pulser 32 to control the starting time of the acoustic wave pulses 18. Reflection wave pulses 24 are reflected at the liquid-air interface 22.

The invention provides a method of acoustic quantity gauging of liquid, such as aircraft fuel, contained in a tank. The time required for an acoustic wave pulse to travel to the reflector 26' (a known distance) and be reflected therefrom and travel to the receiver (a known distance) is measured. The speed of sound in the fuel is determined using the time measured for the acoustic wave pulse to travel the known distances to and from the reference reflector 26'. Fuel level is sensed by transmitting an acoustic wave pulse from the bottom of the tank to the upper surface of the fuel. The signal is reflected from the upper surface of the fuel downwardly to a receiver. The time required for an acoustic wave pulse to travel to and return from the upper surface of the fuel is measured. The level of liquid (fuel) is accurately determined using the speed of sound in the fuel and the time required for an acoustic wave pulse to travel to and from the upper surface of the fuel. The fuel quantity and density are inferred from information stored in memory 68 about the volume of the tank 12 when filled to several levels and the speed of sound in the fuel determined from the measurement of the time for sound to travel the known distance to and from the reference reflector as disclosed by Ellinger et al. in U.S. Pat. No. 4,677,305, the disclosure of which is herein incorporated by reference in its entirety.

With more particular reference to FIG. 2, an electrically passive opto-acoustic liquid quantity gauging system 110 is shown. The electrically passive acoustic fuel quantity gauging system 110 includes a tank 112 which supports acoustic source 114 and an acoustic detector 116. The acoustic source 114 transmits acoustic output pulses 118 through the portion 120' of liquid fuel 120, enclosed by stillwell to the liquid-air interface 122 from which acoustic reflection pulses 124 are reflected to acoustic detector 116. The stillwell 126 is supported by the tank 112 so that the pulses 118 and 124 travel through fuel 120' which is less turbulent in flight than is fuel 120 which is outside of the stillwell 126. Stillwell 126 supports reference reflectors 126'. Fuel flows freely into and out of the stillwell 126 through aperture 128.

The source 114 preferably includes a metal member 130 having a rounded or semispherical (concave or convex) shape supported to allow flexion of the rounded portion. Preferably, at least a portion of the surface of the metal member 130 is nonreflective and black. OPtical pulser 132 pulses high intensity light through optical fiber 134 to the plate 130 which rapidly flexes thereby transmitting acoustic pulses 118. The pulser 132 is preferably a pulsed laser, pulsed laser diode, Q-switched laser or optically pumped Q-switched laser.

The optical source 136 transmits light through optical fiber 138 to acoustic detector 116. Reflected acoustic pulses 124 impinge upon detector 116. The detector 116 is preferably a loop 140 in optical fiber 138. The fiber 138 may be a single mode or multimode. The optical fibers 134, 138 and 142 extend through connectors 139' and 139" and are protected by shielding 139. The output portion, 142 of fiber 138 channels the light to optical detector 144. Detector 144 is connected to signal conditioning electronics 146 by electrical conductor 148. Signal conditioning electronics 146 is connected by electrical conductor 150 to high intensity optical pulser 132. Opto-acoustic signal conditioner 158 includes pulser source 136, detector 144 and signal conditioning electronics 146. Signal conditioning electronics 146 includes analog to digital (A/D) converter 160 which is connected by electrical conductor 148 to detector 144, and by electrical conductor 162 to microprocessor 164. Microprocessor 164 sends and receives signals from memory 168 through electrical conductor 166. Microprocessor 164 sends digital signal through conductor 170 to D/A converter 172. D/A converter 172 sends analog signals through electrical conductor 174 to display 176. Power supply 178 supplies electrical current through electrical Conductor 180 to display 176. Power supply 178 supplies electrical current through electrical conductor 182 to optical pulser 132. Power supply 178 is connected through electrical conductor 184 to optical source 136 and through electrical conductor 186 to A/D converter 160.

By detecting and indicating changes in the light signal from the optical source 136 the return of the reflection pulses is detected and used to indicate the quantity of fuel in tank 112. The optical detector 144, which preferably is a photodetector, receives electromagnetic radiation, such as light from the output portion 142 of optical fiber 138. It will be understood that any type of physical movement of the optical fiber 138, such as slight bending, will have an effect upon the light transmitted therethrough. Various parameters (or properties) of the light can be detected, such as back scattering sites, discontinuities, attenuation, and the like. Changes in properties of the light result from the physical movement of the acoustic waves in the liquid 120' which results in movement of the optical fiber in acoustic detector 116. The optical information is converted to digital form in A/D converter 160 and fed into the microprocessor 164. Fuel quantity measurement signals from the microprocessor 164 are displayed by display 170. Movement of the acoustic detector 116 is monitored by following the corresponding changes in the parameters of the light passing through the fiber 138, which are detected by optical detector 144 and processed in the microprocessor 164. The microprocessor 164 may send further signals to the optical pulser 132 to control the starting time of the acoustic wave pulses 118. Reflected acoustic wave pulses 124 are reflected at the liquid-air interface 122.

In the preferred embodiment of the invention shown in FIG. 2, the sensor system determines the level of a liquid in a container using an opto-acoustic transducer embedded in the bottom of a container. The transducer includes an optical absorber 130 which absorbs the energy of a light pulse transmitted through an optical fiber to the absorber 130 from a source (e.g., a laser) 136 outside of the container. The optical energy is converted to heat in the absorber 130 which undergoes a rapid expansion to generate an acoustic wave pulse 118. The wave pulse 118 propagates upwardly to the surface of the liquid and a reflected wave pulse 124 is reflected downward from the liquid-air interface. The transducer includes acoustic detector (a fiber optic hydrophone) 116 which detects the reflected wave pulse 124. The liquid level is determined as a function of the acoustic pulse propagation time.

In a preferred embodiment of the invention, the change in the intensity of the light transmitted through fiber 138 is monitored by signal conditioning electronics 146. In another preferred embodiment of the invention, the change in the polarization state of the transmitted light is monitored by signal conditioning electronics 146. Alternatively, a interferometrics may be used to monitor the transmitted light.

Tanks in which liquid quantity is measured in accordance with the present invention may be made of metal sheeting, polymeric, (organic or inorganic) composite or other suitable material. Preferred organic polymeric materials include thermoplastic and thermoset polymers. These materials may include a matrix of metal, for example aluminum, thermoplastic such as polyetherether ketone (PEEK), thermoset polymer or ceramic. A preferred composite structure includes high strength filaments or fibers in a polymeric matrix such as a crosslinked epoxy or maleinide.

Epoxy resins are well established for use in making high performance composite structures which include high strength fiber. Preferred fiber materials are metal, glass, boron, carbon, graphite, (continuous or chopped filaments) or the like, such as disclosed by Chu et al in the U.S. Pat. No. 4,677,305. Structures made of these composites can weigh considerably less than their metal counterparts of equivalent strength and stiffness.

The tanks may be fabricated as taught by Gill et al (assigned to Hercules Incorporated) in U.S. Pat. No. 4,581,086. Helical applicators may be used to deposit a ply or plies of continuous filaments into the form of the tank as taught by Gill et al in U.S. Pat. No. 4,519,869 (Assignee, Hercules Incorporated). Alternatively, multiphase epoxy thermosets having rubber within a disperse phase may be used to make tanks, as taught by Bard (assigned to Hercules Incorporated) in U.S. Pat. No. 4,680,076. Optical fibers and transceivers may be embedded in or attached to these tanks during fabrication. Attachment to the tanks of the optical fibers transceivers after construction may be carried out using the same or a different matrix material than is used to fabricate the underlying tanks.

Other matrix compositions which may be used to make tanks in accordance with the present invention include poly(arylacetylene) as disclosed by Jabloner in U.S. Pat. Nos. 4,070,333; and 4,097,460; and French in U.S. Pat. No. 4,144,218 (each assigned to Hercules Incorporated). Chu, et al. in U.S. Pat. No. 4,656,208, (assigned to Hercules Incorporated), discloses thermosetting epoxy resin compositions and thermosets therefrom.

Various further applications and modifications falling within the scope and spirit of this invention will occur to those skilled in the art. The method and system of the invention accordingly are not to be thought of as limited to the specific embodiments disclosed which are set forth merely for illustrative purposes.

What is claimed is:

1. An optically controlled acoustic transmission and reception system, comprising:
   a tank,
   an electrically passive optically controlled acoustic transmitter,
   an electrically passive acoustic receiver,
   a first and a second source of electromagnetic radiation,
   a first and a second optical fiber,
   said transmitter being positioned to transmit acoustic waves into said tank,
   said first optical fiber being connected to said transmitter and to said first source of electromagnetic radiation, said receiver being connected to said second optical fiber, said transmitter being adapted to convert said electromagnetic radiation into acoustic pulses, said receiver being adapted to modulate electromagnetic radiation from said second source passing through said second optical fiber in response to said acoustic pulses, whereby said acoustic pulses from said transmitter are received by said receiver.

2. The system of claim 1, wherein said system further comprises a detector, and said second optical fiber is connected to said detector, said detector being adapted to defect said electromagnetic radiation passing through said second optical fiber.

3. The system of claim 1 wherein said system further comprises a detector, an analog to digital converter, a microprocessor and a display, and wherein said detector is connected to said second optical fiber and to said converter, said converter is connected to said microprocessor and said microprocessor is connected to said display, said modulated light from said second optical fiber being detected by said detector, said detector providing a signal to said converter, said converter providing a signal to said microprocessor, said microprocessor providing a signal representative of fuel quantity to said display, whereby the quantity of fuel in said tank is displayed.

4. An electrically passive optically activated transducer, comprising:
   a first and a second optical fiber,
   a flexible member adapted to vibrate and thereby provide acoustic waves in response to impingement thereon of pulsed electromagnetic radiation from said first optical fiber, said second optical fiber being adapted to modulate electromagnetic radiation passing through said second optical fiber in response to the impingement of said acoustic waves on said second optical fiber.

5. The transducer of claim 4 further comprising a first and a second source of electromagnetic radiation, said first source of electromagnetic radiation being adapted to transmit radiation into said first optical fiber, said second source of electromagnetic radiation being adapted to transmit light into said second optical fiber.

6. An electrically passive optically activated system, comprising a first and a second optical fiber, a source of pulsed infrared radiation, a source of visible light and a flexible member adapted to vibrate and thereby provide acoustic pulses in response to impingement of pulsed infrared radiation thereon said source of infrared radiation being adapted to transmit pulses of infrared radiation into said first optical fiber, said acoustic pulses from said flexible member being reflected to said second optical fiber, said source of visible light being adapted to transmit visible light into said second optical fiber, said second optical fiber being adapted to modulate said visible light passing through said second optical fiber in response to said reflected acoustic pulses.

7. The system of claim 6 further comprising a tank, said tank enclosing a chamber, said flexible member being adapted to transmit said acoustic pulses into said chamber, said second optical fiber being adapted to modulate said visible light passing through said second fiber in response to said acoustic pulses traveling within said chamber.

8. An electrically passive method of optically controlling acoustic transmission comprising:
   (a) providing a tank enclosing a chamber, an electrically passive optically controlled acoustic transmitter, a first source of electromagnetic radiation, a first optical fiber, said transmitter being positioned to transmit acoustic waves into said tank, said optical fiber being connected to said transmitter and to said first source of electromagnetic radiation, said transmitter being adapted to convert said electromagnetic radiation into acoustic pulses, and
   (b) transmitting electromagnetic radiation from said first source through said first fiber whereby acoustic waves are transmitted from said acoustic transmitter.

9. The method of claim 8 further comprising
   providing an electrically passive acoustic receiver, and a second source of electromagnetic radiation, said receiver comprising at least a portion of a second optical fiber,
   said receiver being positioned to receive acoustic waves from said tank, said receiver being connected to said second optical fiber, said receiver being adapted to modulate electromagnetic radiation from said second source passing through said second optical fiber in response to said acoustic waves whereby said acoustic waves are received by said receiver.

10. The method of claim 9 wherein said method further comprises providing a detector, and said second optical fiber is connected to said detector, said detector being adapted to an electrical signal in response to electromagnetic radiation passing through said second optical fiber.

11. The method of claim 10 wherein said method further comprises providing an analog to digital converter, a microprocessor and a display, and wherein said detector is connected to said converter, said converter is connected to said microprocessor and said microprocessor is connected to said display, said detector providing a signal to said converter, said converter providing a signal to said microprocessor, said microprocessor providing a signal representative of fuel quantity to said display, whereby the quantity of fuel in said tank is displayed.

12. The method of claim 8 wherein said electromagnetic radiation transmitted from said first source is infrared radiation.

13. The method of claim 9 wherein said electromagnetic radiation from said first source is visible light.

14. The method of claim 9 further comprising providing a stillwell said stillwell enclosing a passage, said stillwell being positioned in said chamber and connected to said tank, said transmitter being adapted to transmit acoustic waves into said passage.

15. The method of claim 14 further comprising
   providing an electrically passive acoustic receiver, and a second source of electromagnetic radiation, said receiver comprising at least a portion of a second optical fiber,
   said receiver being positioned to receive acoustic waves from said tank, said receiver being connected to said second optical fiber, said receiver being adapted to modulate electromagnetic radiation from said second source passing through said second optical fiber in response to said acoustic waves whereby said acoustic waves are received by said receiver.

16. The method of claim 15 wherein said receiver is positioned to receive acoustic waves traveling in said passage.

17. An electrically passive method of optically activating an acoustic transmitter for transmission of acoustic waves into a liquid enclosed by a tank comprising:
   (a) providing a tank, an optical fiber,
      a transducer comprising a flexible member adapted to vibrate in response to impingement of pulsed electromagnetic radiation thereon, said tank enclosing a liquid, said first optical fiber being adapted to pass electromagnetic radiation onto said flexible member, and
   (b) passing electromagnetic radiation from an electromagnetic radiation source through said optical fiber onto said flexible member whereby said transducer transmits acoustic waves into said liquid.

18. The method of claim 17 wherein said flexible member has a black coating.

19. The method of claim 17 further comprising: providing a detector, and wherein said tank encloses air, and said air and said gas form a liquid-air interface, a portion of said acoustic waves being reflected from said liquid-air interface to said detector, said detector being adapted to detect said reflected acoustic waves.

20. The method of claim 19 further comprising liquid quantity determining means to determine the quantity of said liquid in said tank, said liquid quantity determining means being connected to said electromagnetic radiation source and to said detector.

21. An electrically passive method of fuel quantity measurement comprising (a) providing a tank enclosing liquid fuel said fuel having air-liquid interface,
(a) providing a first optical fiber,
a flexible member adapted to vibrate in response to impingement of pulsed electromagnetic radiation thereon, said first optical fiber being adapted to pass electromagnetic radiation onto said flexible member,
(b) passing electromagnetic radiation through said fiber optical fiber onto said flexible member whereby said transducer transmits acoustic waves,
providing an electrically passive acoustic receiver, and a second source of electromagnetic radiation, said receiver comprising at least a portion of a second optical fiber,
said receiver being positioned to receive acoustic waves from said tank, said receiver being connected to said second optical fiber, said receiver being adapted to modulate electromagnetic radiation from said second source passing through said second optical fiber in response to said acoustic waves whereby said acoustic waves are received by said receiver,
measuring the time period required for said acoustic waves to travel to said air-liquid interface and back to said receiver, and
determining the quantity of said liquid fuel from said time period and information relating liquid quantity in said tank to said time period.

22. The method of claim 21 further comprising providing a microprocessor and a memory and wherein said information relating liquid quantity to said time period is stored in said memory, and said determination of fuel quantity is made in said microprocessor.

23. An electrically passive system for liquid quantity determination, comprising:
a tank,
an electrically passive optically controlled acoustic transmitter, said transmitter comprising an optical fiber,
an optical source,
an acoustic detector,
microprocessor,
said optical source and said acoustic detector being connected to said microprocessor,
said optical source being connected to said optical fiber,
said tank being adapted to enclose liquid and air, said liquid and air having a liquid-air interface,
said transmitter being adapted to transmit initial acoustic waves through said liquid to said liquid-air interface,
a portion of said initial acoustic waves being reflected from said liquid-air interface,
said acoustic detector being adapted to detect said reflected acoustic waves,
said microprocessor being adapted to determine the quantity of said liquid in said tank.

24. The system of claim 23 wherein said liquid is a fuel.

25. The system of claim 24 wherein said acoustic detector is electrically passive.

26. The system of claim 23 further comprising a display, said display being connected to said microprocessor, said display being adapted to display said quantity of said liquid in said tank.

* * * * *